United States Patent [19]

Howarth

[11] 4,276,418
[45] Jun. 30, 1981

[54] PROCESS FOR THE PURIFICATION OF ESTERS OF PHOSPHORUS THIOACIDS

[75] Inventor: Michael S. Howarth, Oldham, England

[73] Assignee: Imperial Chemical Industries Limited, London, England

[21] Appl. No.: 116,596

[22] Filed: Jan. 28, 1980

[30] Foreign Application Priority Data

Feb. 19, 1979 [GB] United Kingdom ............... 05739/79

[51] Int. Cl.³ ............................................... C07F 9/65
[52] U.S. Cl. .................................. 544/243; 260/963; 260/989; 260/990
[58] Field of Search ....................... 260/989, 990, 963; 544/243

[56] References Cited

U.S. PATENT DOCUMENTS 2,770,567  11/1956  Wedemeyer et al. ............... 260/989
3,590,104  6/1971   Hanna ................................. 260/973

OTHER PUBLICATIONS

Kovacicova et al., "Pesticide Science", vol. 2, (1971) p. 101.
Umetsu et al., "J. Agric. Food Chem.", vol. 25, (1977) p. 946.
Takeshi, "Chemical Abstracts", vol. 57, (1962), 2625i.

*Primary Examiner*—Anton H. Sutto
*Attorney, Agent, or Firm*—Cushman, Darby & Cushman

[57] ABSTRACT

A process for the purification of esters of phosphorus thioacids having the formula:

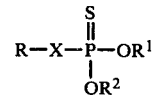

wherein
R is an organic radical which is attached via a carbon atom thereof to X;
$R^1$ and $R^2$ are optionally substituted hydrocarbon radicals which may be the same or different, and
X is O or S, and which contains as an impurity a thiolo isomer having the formula:

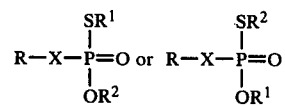

in which R, $R^1$, $R^2$ and X have the previously defined meanings, which comprises washing the ester with an aqueous solution of an acid or an acid salt.

Particularly applicable to esters in which R is a substituted pyrimidinyl, phenyl or benzyl radical and $R^1$ and $R^2$ are alkyl radicals containing from 1 to 4 carbon atoms, especially methyl or ethyl radicals, which are useful as insecticides.

5 Claims, No Drawings

PROCESS FOR THE PURIFICATION OF ESTERS OF PHOSPHORUS THIOACIDS

This invention relates to a process for the purification of esters of phosphorus thioacids.

Esters of phosphorus thioacids having the general formula:

$$R-X-\underset{OR^2}{\underset{|}{\overset{\overset{S}{\|}}{P}}}-OR^1 \qquad (I)$$

wherein R is an organic radical which is attached via a carbon atom thereof to X, $R^1$ and $R^2$ are optionally substituted hydrocarbon radicals which may be the same or different, and X is O or S, may be prepared by reaction of a compound of the formula:

$$\text{halogen}-\underset{OR^2}{\underset{|}{\overset{\overset{S}{\|}}{P}}}-OR^1 \qquad (II)$$

with a compound of the formula R—XH in the presence of an acid-binding agent.

The organic radical R may be a hydrocarbon radical, for example, an alkyl, cycloalkyl, aralkyl, alkaryl, alkenyl or aryl radical which may be further substituted, or it may be a heterocyclic radical.

The halogen atom in the compound of formula (II) may be for example, a bromine atom and especially a chlorine atom.

The acid-binding agent which is used in the above-mentioned process may be, for example, an alkali or alkaline earth metal carbonate such as calcium carbonate, sodium carbonate and especially potassium carbonate, or an alkali metal hydroxide such as sodium hydroxide or potassium hydroxide.

The reaction is preferably carried out in the presence of an inert organic solvent, which may be, for example, a hydrocarbon, halogenated hydrocarbon, ester, ketone or ether. Examples of suitable solvents are hexane, cyclohexane, toluene, xylene, monochlorobenzene, butyl acetate, 2-ethoxyethyl acetate, methyl isobutyl ketone and dioxan.

The reaction is carried out at a moderately elevated temperature, for example, up to 100° C., conveniently at 55°-60° C., for a reaction time of 0.5 to 24 hours.

When prepared in this way the esters of formula (I) generally contain as an impurity the corresponding thiolo isomer having the formula:

$$R-X-\underset{OR^2}{\underset{|}{\overset{\overset{SR^1}{|}}{P}}}=O \quad \text{or} \quad R-X-\underset{OR^1}{\underset{|}{\overset{\overset{SR^2}{|}}{P}}}=O$$

in which R, $R^1$, $R^2$ and X have the previously defined meanings. The amount of thiolo impurity does not usually exceed 5% by weight of the total ester and is generally present to the extent of 1-2% by weight. The presence of the thiolo isomer in the normal ester can be detected and estimated by appropriate analytical means, for example, gas-liquid chromatographic (GLC) analysis. The presence of the thiolo ester has the disadvantage that the compound is unstable and in the presence of traces of moisture decomposes to produce volatile sulphur compounds (e.g. alkyl mercaptans) having an objectionable odour.

The esters of formula (I) are themselves known to undergo slow isomerisation in the presence of traces of nucleophiles to give the corresponding thiolo isomers having the above-defined structure, so that even pure ester may eventually develop the odour of volatile sulphur compounds. This isomerisation can be prevented by incorporating into the ester of formula (I) a stabiliser which may be, for example, epichlorohydrin, a p-benzoquinone, a chelate compound of aluminium with a β-ketoester or a β-diketone, for example, aluminium acetylacetonate, or an epoxidised oil such as epoxidised linseed oil or epoxidised soya bean oil. These stabiliser compounds are valuable in preventing further deterioration in esters of formula (I) after they have been prepared, but are of no effect against the thiolo isomers which have been formed as a by-product in the normal course of the process by which the esters are manufactured.

It has now been found that the thiolo isomer content of esters of formula (I) can be reduced to a level at which objectionable odours do not develop, by giving the ester a simple wash treatment.

According to the present invention there is provided a process for the purification of esters of phosphorus thioacids having the formula:

$$R-X-\underset{OR^2}{\underset{|}{\overset{\overset{S}{\|}}{P}}}-OR^1 \qquad (I)$$

wherein R, $R^1$, $R^2$ and X have the previously defined meanings which comprises washing the ester with an aqueous solution of an acid, whereby the content of thiolo impurity in the ester is reduced to a level at which the subsequently stabilised ester does not develop objectionable odours on storage.

The term "acid" also includes acid salts, and examples of the acids which may be used in the above process are sulphuric acid, sodium hydrogen sulphate, potassium hydrogen sulphate, sodium metabisulphite, hydrochloric acid, acetic acid and orthophosphoric acid.

For fully satisfactory results the thiolo isomer content of the purified ester should not exceed 0.3% by weight, and preferably should not exceed 0.1% by weight of the total ester.

The aqueous solution of acid which is employed in the process may contain from 1 to 10% by weight of the acid, the most satisfactory results generally being obtained with a solution containing from 3 to 5% by weight of acid.

More than one wash treatment may be necessary to achieve the desired low level of thiolo isomer in the final product, but it is not usually necessary to employ more than four washes with aqueous acid.

It is convenient and more efficient to wash with aqueous acid the solution of the phosphorus thioacid ester in an inert organic solvent as obtained at the end of the process of preparation, provided that the solvent is one which is immiscible with water. In this case the volume of aqueous acid which is used is conveniently one half to one third of the volume of the solution being washed. The washing treatment may be carried out at normal room temperature, for example, 15° to 25° C., or at a slightly elevated temperature, for example 35° to 40° C. Instead of batchwise washing with several separate portions of aqueous acid, the solution of the ester in a water-immiscible inert organic solvent may be subjected to a continuous washing procedure, for example, using a counter-current method.

After the acid washing treatment has been completed the solution of the ester in organic solvent may be given a wash with aqueous sodium bicarbonate solution to neutralise residual acid, and then a final water wash. The purified ester is isolated from its solution in organic solvent by conventional means i.e. removal of the solvent by evaporation or distillation if desired under reduced pressure, a procedure which also serves to remove any residual water from the solution by azeotropic distillation.

The purified ester is then treated with a stabiliser, for example, one of the stabilisers already mentioned, in order to minimise any decomposition which may give rise to formation of thiolo isomer.

The present process is particularly valuable for the treatment of esters of formula (I) in which R is a substituted pyrimidinyl, phenyl or benzyl radical and $R^1$ and $R^2$ are alkyl radicals containing from 1 to 4 carbon atoms, especially methyl or ethyl radicals. These esters are useful as insecticides and are described in, for example, U.K. Pat. Nos. 1,019,227, 1,203,026, 1,204,552, 1,205,000 and 1,384,401.

Examples of such compounds, with their common names where applicable are given in the following table:

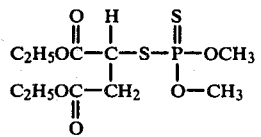 Malathion

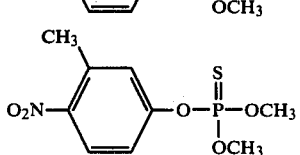 Methyl Parathion

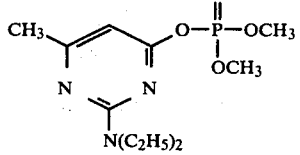 Fenitrothion

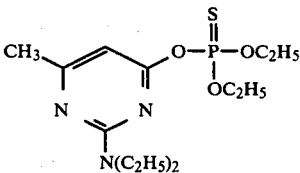 Pirimiphos-methyl

Pirimiphos-ethyl

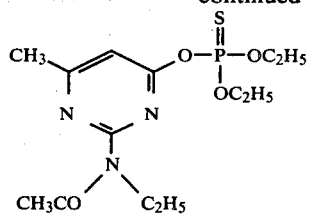

The tendency of these compounds to develop objectionable odours on storage makes them unacceptable for certain uses, for example, domestic and public health applications, and the present process enables this defect to be substantially overcome.

The invention is illustrated by the following Example, in which parts and percentages are by weight.

EXAMPLE

Preparation of Pirimiphos-Methyl with Work-Up Modified to Remove Thiolo Isomer
[O,S-Dimethyl-O-[2-(Diethylamino)-6-methyl-4-pyrimidinyl]phosphorothioate]

To a mixture of 62 parts of methyl isobutyl ketone and 29 parts of anhydrous potassium carbonate in a stirred reaction vessel was first added 27 parts of 2-(diethylamino)-4-hydroxy-6-methyl pyrimidine. After heating the mixture to 55° C. the addition of 25 parts of dimethylphosphorochlorido thionate was commenced. The reaction is exothermic and the addition was made at a rate such that the temperature of the reaction did not exceed 60° C. When the addition was finished the reaction mixture was maintained at 55°–60° C. for 2 hours, then cooled to ambient temperature. 70 Parts of water were added and after 10 minutes stirring the aqueous layer was separated and discarded. The organic layer was given four successive washes with 5% w/w aqueous sulphuric acid, the first wash being with 50 parts of aqueous acid and the succeeding washes using 30 parts of aqueous acid. The washing was accomplished by stirring the acid with the organic layer at 35° C. in a reaction vessel for 10 minutes at such a speed that the acid and organic layers were efficiently intermingled. After the final acid wash the organic layer was washed with 10 parts of 2.5% aqueous sodium bicarbonate solution and then with 10 parts of water. The pirimiphos-methyl was isolated by taking the organic solution after water washing and removing the methyl isobutyl ketone by vacuum distillation.

The pirimiphos-methyl produced by this procedure contained less than 0.1% of thiolo isomer.

When a similar preparation was performed and only water washing was employed in the work-up the product contained 4.5% of thiolo isomer.

When a similar preparation was performed in which 3 acid washes were given, the first of 30 parts of 3.2% aqueous sulphuric acid the second and third of 30 parts of 1.2% aqueous sulphuric acid, the product contained 1.3% thiolo isomer.

When a similar preparation was performed in which 4 acid washes were given, the first of 30 parts 3.2% aqueous sulphuric acid and the second, third and fourth washes with 30 parts of 1% aqueous sulphuric acid the product contained 0.7% of thiolo isomer.

The effect of reducing the thiolo isomer content of pirimiphos-methyl on methyl mercaptan evolution is shown in the following table.

| Table Illustrating the Reduced Evolution of Methyl Mercaptan by Samples of Pirimiphos-Methyl with Low Thiolo Isomer Content | |
| --- | --- |
| % Thiolo Isomer in Pirimiphos-Methyl upon Isolation. | Methyl Mercaptan Generated During Standard Accelerated Storage Trial (p.p.m.) |
| 1.3 | 85 |
| 1.0 | 45 |
| 0.7 | 25 |
| 0.3 | 5 |
| <0.1 | 5 |

STANDARD ACCELERATED STORAGE TRIAL

A sample of the material test in a sealed glass bottle, is kept in an incubator at 37° C. for 8 weeks. The bottle is then opened and the stored material is analysed by some suitable method (e.g. GLC) to determine the amount of mercaptan present.

I claim:

1. A process for the purification of esters of phosphorus thioacids having the formula:

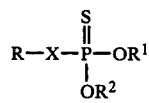

wherein

R is an organic radical which is attached via a carbon atom thereof to X;

$R^1$ and $R^2$ are optionally substituted hydrocarbon radicals which may be the same or different, and X is O or S, and which contains as an impurity a thiolo isomer having the formula:

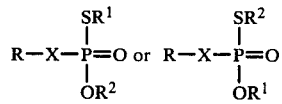

in which R, $R^1$, $R^2$ and X have the previously defined meanings, which comprises washing the ester with 1 to 5% by weight aqueous sulfuric acid whereby the content of thiolo impurity in the ester is reduced to a level at which the subsequently stabilized ester does not develop objectionable odors on storage.

2. A process as claimed in claim 1 wherein the ester is given up to four washes with said aqueous sulfuric acid.

3. A process as claimed in claim 1 wherein the ester, in the form of a solution in a water-immiscible inert organic solvent, is washed with said aqueous sulfuric acid in amount of from one half to one third of the volume of solution being washed.

4. A process as claimed in claim 1 wherein the amount of thiolo isomer remaining in the purified ester does not exceed 0.3% by weight.

5. A process as claimed in claim 1 wherein the amount of thiolo isomer remaining in the purified ester does not exceed 0.1% by weight.

* * * * *